(12) United States Patent
Ando

(10) Patent No.: US 7,479,388 B2
(45) Date of Patent: Jan. 20, 2009

(54) APPARATUS FOR INJECTING SOLUTION INTO CELL

(75) Inventor: Moritoshi Ando, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 648 days.

(21) Appl. No.: 10/928,930

(22) Filed: Aug. 30, 2004

(65) Prior Publication Data

US 2005/0244948 A1 Nov. 3, 2005

(30) Foreign Application Priority Data

Apr. 28, 2004 (JP) ............................. 2004-133791

(51) Int. Cl.
C12M 1/00 (2006.01)
C12M 3/00 (2006.01)
(52) U.S. Cl. .................. 435/285.1; 435/285.2; 435/467
(58) Field of Classification Search ................ 435/461, 435/173, 240.1, 285.2, 285.1
See application file for complete search history.

(56) References Cited

U.S. PATENT DOCUMENTS

| | | | |
|---|---|---|---|
| 5,013,660 A | 5/1991 | Kasuya et al. | |
| 5,240,842 A | 8/1993 | Mets | |
| 5,702,359 A | 12/1997 | Hoffmann et al. | |
| 5,993,434 A | 11/1999 | Dev et al. | |
| 6,008,038 A | 12/1999 | Kröger et al. | |
| 6,174,675 B1 * | 1/2001 | Chow et al. | 435/6 |
| 7,011,382 B2 * | 3/2006 | Holm et al. | 347/9 |
| 2002/0019052 A1 * | 2/2002 | Nolan et al. | 435/461 |
| 2002/0115219 A1 | 8/2002 | Kobayashi et al. | |
| 2003/0180073 A1 | 9/2003 | Ishiyama et al. | |
| 2005/0277182 A1 * | 12/2005 | Ando et al. | 435/285.2 |

FOREIGN PATENT DOCUMENTS

| | | |
|---|---|---|
| JP | 60-118473 | 6/1985 |
| JP | 63-222680 | 9/1988 |
| JP | 64-3560 | 1/1989 |
| JP | 64-38146 | 2/1989 |
| JP | 64-38147 | 2/1989 |
| JP | 64-38148 | 2/1989 |
| JP | 64-34610 | 3/1989 |
| JP | 1-112976 | 5/1989 |

(Continued)

OTHER PUBLICATIONS

Furth et al. Gene transfer into mammalian cells by jet injection. 1995. Hybridoma, v.14 N. 2, pp. 149-152.*

(Continued)

Primary Examiner—Walter D Griffin
Assistant Examiner—Shanta G Doe
(74) Attorney, Agent, or Firm—Westerman, Hattori, Daniels & Adrian, LLP.

(57) ABSTRACT

An apparatus of the invention is for injecting a solution into a cell. The apparatus includes a nozzle that jets a solution to a cell, and a laser irradiating unit that irradiates a laser to the cell to form an opening through which the solution jet from the nozzle is introduced into the cell. The nozzle jets the solution toward a nucleus of the cell, and the laser forms the opening in the cell at a point in a cell membrane of the cell such that the solution can be applied on the nucleus.

9 Claims, 13 Drawing Sheets

FOREIGN PATENT DOCUMENTS

| | | |
|---|---|---|
| JP | 1-235575 | 9/1989 |
| JP | 2-119770 | 5/1990 |
| JP | 3-119989 | 5/1991 |
| JP | 3-259076 | 11/1991 |
| JP | 4-349889 | 12/1992 |
| JP | 5-192171 | 8/1993 |
| JP | 6-62871 | 3/1994 |
| JP | 6-343478 | 12/1994 |
| JP | 8-290377 | 11/1996 |
| JP | 9-248183 | 9/1997 |
| JP | 10-165166 | 6/1998 |
| JP | 11-18770 | 1/1999 |
| JP | 11-506630 | 6/1999 |
| JP | 11-347971 | 12/1999 |
| JP | 2000-23657 | 1/2000 |
| JP | 2001-252065 | 9/2001 |
| JP | 2001-513439 | 9/2001 |
| JP | 2002-18800 | 1/2002 |
| JP | 2002-27969 | 1/2002 |
| JP | 2002-500946 | 1/2002 |
| JP | 2002-65241 | 3/2002 |
| JP | 2002-526103 | 8/2002 |
| JP | 2002-325572 | 11/2002 |
| JP | 2003-070468 | 3/2003 |
| JP | 2003-93898 | 4/2003 |
| JP | 2003-125750 | 5/2003 |
| WO | WO 99/10099 | 3/1999 |
| WO | WO 99/37400 | 7/1999 |
| WO | WO 00/20554 | 4/2000 |
| WO | WO 00/34436 | 6/2000 |

OTHER PUBLICATIONS

Tirlapur et al. Femtosecond near-infrared laser pulses as a versatile non-invasion tool for intra-tissue nanoprocessing in plants without compromising viability. 2002. The plant Journal, v.31, N. 3, pp. 365-374.*

European Search Report dated Feb. 7, 2006.

* cited by examiner

APPARATUS FOR INJECTING SOLUTION INTO CELL

BACKGROUND OF THE INVENTION

1) Field of the Invention

The present invention relates to an apparatus for injecting a solution into a cell. The solution is, for example, a gene solution or a drug solution.

2) Description of the Related Art

Recently, in the field of life science, specifically in the fields of the regenerative medicine and the genome-based drug discovery, by injecting a gene or a drug into a cell, modification of property of the cell is practiced. Such a technology enables to elucidate a function of a gene, and also enables a tailor-made medicine for providing a care suitable for a genetic characteristic of an each individual.

To produce such cells, various solution injecting technologies have been proposed. Specifically, there are a biological method such as a virus vector method, a chemical method such as a lypofection method, an electric method such as an electroporation method, a physical method such as a particle gun method, an optical method such as a laser injection method, and a mechanical method such as a microinjection method.

The virus vector method is a method for gene transfer to a cell in which a genetically modified virus is produced, and by the infection mechanism of the genetically modified virus, the gene transfer is carried out. The lypofection method is a method in which an electrically charged liposome and a DNA are combined, and by making it adsorb on the surface of a cell, the DNA is transferred into the cell. However, such biological method and the chemical method have disadvantages. There is a great limitation on combinations of a cell and a transfer substance in these methods. Especially, the virus vector method has a disadvantage in which danger of causing infectious diseases is relatively high because a cell that has strong infectivity is used.

The electroporation method is a method in which a gene solution or a drug solution is injected through a hole of a cell membrane that is formed by rupturing the cell membrane with an electric pulse. The particle gun method is a method for the gene transfer in which a cell membrane is ruptured by shooting a cell with the minute particle to which a gene is adhered to transfer the gene into the cell. Although the electric method and the physical method have an advantage in which combinations of the cell and the transfer substance are not limited, these methods also have a problem in which success rate of the gene transfer stays low at several percent because control of an apparatus is difficult, and there are cases in which the cell membrane cannot be properly ruptured, or the cell membrane is ruptured too much resulting death of the cell.

On the other hand, the optical method such as the laser injection method and the mechanical method such as the microinjection method have been receiving attention because these methods have high success rate and they are safe.

In the laser injection method, a drug solution is dissolved in a cultivation solution of the cell, and an opening is formed in a cell membrane of the cell by irradiating a laser. The drug solution seeps into the cell by the Brownian movement (refer, for example, to the patent literature 1). This method has an advantage in which the solution injection according to a microscopic structure of the cell is possible because the cell membrane is ruptured by the laser.

In the microinjection method, a drug solution is filled in a thin needle that has a diameter of 1 micrometer (μm) or less, and by injecting the needle into a cell, the drug solution is injected into the cell (refer, for example, to the patent literature 2). In this method, the needle tip can be controlled to minimize damage to the cell by carrying out the injection under a microscope by a skilled operator, and with a control device that has high resolution. Therefore, nearly 100% success rate can be obtained. This method also has an advantage in which this method does not limit a combination of the cell and the transfer substance.

Patent Literature 1: Japanese Patent Application Laid-Open No. 2003-70468

Patent Literature 2: Japanese Patent Application Laid-Open No. H8-290377

However, the laser injection method limits concentration and kind of the drug solution because the Brownian movement is used as a prime mover for the drug solution to seep into the cell. Moreover, the use of the Brownian movement as the prime mover leads to a low introducing efficiency in introducing the drug solution because directions of movement of drug molecules are irregular. Therefore, a large amount of the drug solution, which is expensive, is necessary, and the injection by this method costs a lot.

In the microinjection method, when a same needle is repeatedly used, a part of the cell membrane sticks to the needle. As a result, the tip of the needle becomes thick, and the needle becomes unusable. Moreover, to pierce through the cell membrane with the needle, the needle has to be injected keeping some amount of momentum. Therefore, it is impossible to carry out the injection according to the microscopic structure of the cell. For example, cytoplasm of a suspended cell has thickness of only 1 μm to 2 μm, therefore, it is difficult to set the tip of the needle on this part to carry out the injection.

SUMMARY OF THE INVENTION

It is an object of the present invention to provide a cheaper apparatus for injecting a solution into a cell.

An apparatus according to an aspect of the present invention is for injecting a solution into a cell. The apparatus includes a solution jetting unit that jets a solution toward a cell; and a laser irradiating unit that irradiates a laser to the cell to form an opening in the cell through which the solution jet by the solution jetting unit is introduced into the cell.

The other objects, features and advantages of the present invention are specifically set forth in or will become apparent from the following detailed descriptions of the invention when read in conjunction with the accompanying drawings.

DETAILED DESCRIPTION

Exemplary embodiments of an apparatus for injecting a solution into a cell according to the present invention are explained in detail below with reference to the accompanying drawings.

Figure 1:
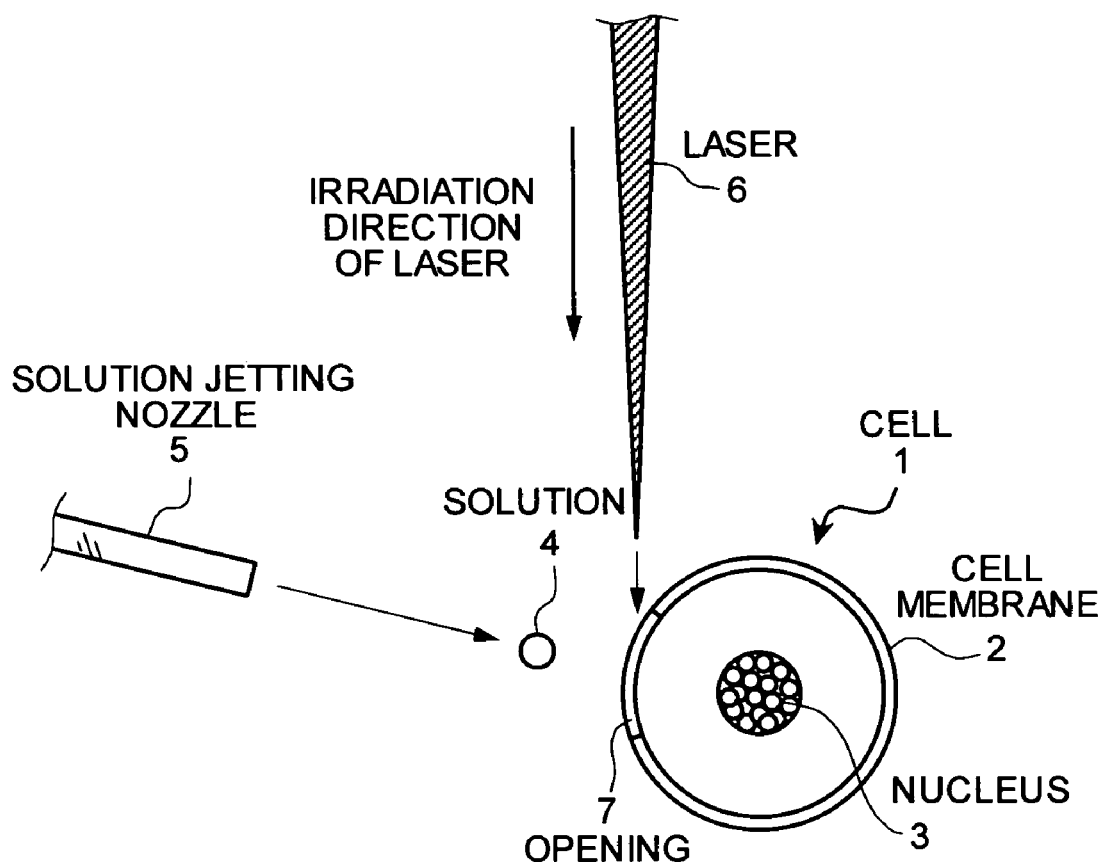
FIG. 1 is a diagram for explaining a concept of solution injection by an apparatus for injecting a solution into a cell according to the present invention.

An overview of solution injection by the apparatus for injecting a solution into a cell according to the present invention is explained first. FIG. 1 is a diagram for explaining a concept of the solution injection by the apparatus according to the present invention. A cell 1 includes a cell membrane 2, and a nucleus 3. A solution 4 is to be injected in the cell 1, precisely, between the cell membrane 2 and the nucleus 3, or preferably inside the nucleus 3. For this purpose, first, the solution 4 is jet from a solution jetting nozzle 5 toward the cell 1. Before the solution 4 reaches the cell membrane 2, a laser 6 is irradiated to the cell membrane 2 to form an opening 7 in the cell membrane 2. Thus, the solution 4 can be injected inside the cell membrane through the opening 7.

In which direction the laser 6 should be irradiated is explained below. Basically, the direction in which the laser 6 is irradiated may be arbitrarily determined as long as the opening 7 is formed in the cell membrane 2 by the laser in such a manner that the solution 4 can be injected into the cell 1 through the opening 7. It is preferable that the laser is irradiated in such a manner that the opening 7 is formed at a portion to which the solution 4 is jet on the cell membrane 2 of the cell 1 from the solution jetting nozzle 5. This enables to inject the solution 4 inside the cell 1 through the opening 7 without being blocked by the cell membrane 2.

If the laser 6 is irradiated to the cell 1 in a direction of a line that connects the cell membrane 2 and the nucleus 3, while making an opening in the cell membrane 2, the laser can damage even the nucleus 3. In such a case the cell 1 may die. Therefore, it is preferable that the laser 6 is irradiated in a direction that is substantially perpendicular to a line that connects the nucleus 3 of the cell 1 and a point on a surface of the cell 1 at which the opening 7 is to be formed ("irradiation direction of the laser" shown in FIG. 1). Thus, the laser 6 will only make an opening to the cell membrane 2 and will not damage the nucleus 3. It is preferable that the opening 7 is formed so as to enable smooth injection of the solution 4 into the cell 1 while minimizing the damage to the cell 1. For this purpose, the diameter of the opening should be substantially as large as a diameter of the solution 4 jet, or a little bit larger than the diameter of the solution 4 jet.

In which direction the solution 4 should be jet is explained below. Basically, the direction in which the solution 4 should be jet may be arbitrarily determined as long as the solution 4 is injected into the cell 1 through the opening 7 formed in the cell membrane 2 by the laser. It is preferable that the solution 4 is jet in a direction of the line that connects the nucleus 3 of the cell 1 and the point on a surface of the cell 1 at which the opening 7 is to be formed, which is a direction that is substantially perpendicular to the direction in which the laser 6 is irradiated. This enables to jet the solution 4 to the opening 7 formed in the cell 1 from the front to efficiently inject the solution 4 into the cell 1.

At what timing the laser 6 should be irradiated is explained next. The laser 6 is irradiated to the cell membrane 2 to form the opening 7 when the solution 4 jet reaches the cell membrane 2. However, strictly speaking, if the laser 6 is irradiated at the moment the solution 4 reaches the cell membrane 2, the solution 4 may reach the cell membrane 2 before the opening 7 is completely formed. Therefore, it is preferable that the laser 6 is irradiated a predetermined time before the solution 4 reaches the cell membrane 2 considering time that is required for the laser 6 to be applied and for the solution 4 to reach the cell membrane 2. On the other hand, if the opening 7 is formed too early, the opening 7 may become smaller, due to self-repair mechanism of the cell 1, before the solution 4 reaches the opening 7, and the solution 4 may not penetrate into the cell 1. Because of the problems above, it is preferable that the irradiation of the laser 6 is carried out at a point of time that is before the solution 4 reaches the cell membrane 2, and that enables the solution to be injected before the opening to be formed in the cell becomes smaller by a self-repair mechanism of the cell, for example, before several microseconds (μs) before the solution 4 reaches the cell membrane 2.

Figure 2:
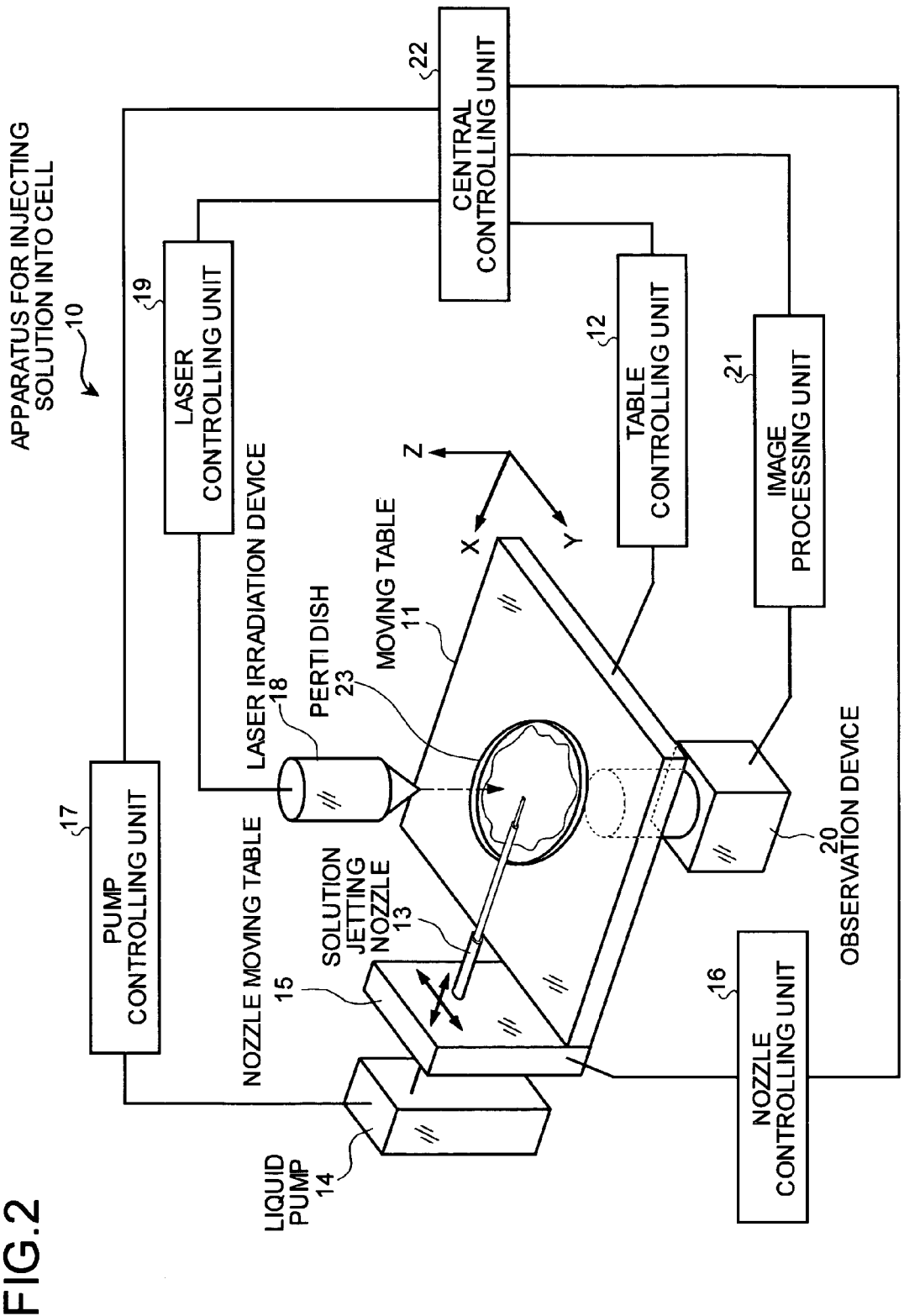
FIG. 2 is a configuration of the apparatus according to a first embodiment.

An apparatus for injecting a solution into a cell according to a first embodiment is explained next. FIG. 2 is a configuration of an apparatus 10 for injecting a solution into a cell according to the first embodiment. The apparatus 10 includes a moving table 11, a table controlling unit 12, a solution jetting nozzle 13, a liquid pump 14, a nozzle moving table 15, a nozzle controlling unit 16, a pump controlling unit 17, a laser irradiation device 18, a laser controlling unit 19, an observation device 20, an image processing unit 21, and a central controlling unit 22. The XYZ coordinate system shown in FIG. 2 will be used for the explanation below. In other words, X and Y directions are in the plane of the moving table 11, and Z direction is perpendicular to both the X and Y directions.

The moving table 11 is a unit to change a position of the cell 1, and is movable in the directions X and Y. A specific structure of the moving table 11 is arbitrary. For example, the moving table 11 may be structured as a flat board that is formed with a transparent material, such as glass and polycarbonate, so as to enable observation of the cell 1 (not shown), by the observation device 20 explained later, from an opposite side of the moving table 11 to a side on which the cell 1 is arranged. A petri dish 23 is placed on the moving table 11. A cell cultivation solution is put in the petri dish 23, and the cell 1 is anchored on a surface inside the petri dish 23. The cell 1 may be anchored by any known method. For example, the cell 1 may be anchored with a cell adhesive, or by sucking with a suction device. The table controlling unit 12 controls the movement of the moving table 11 based on an instruction from the central controlling unit 22.

The solution jetting nozzle 13 and the liquid pump 14 are a solution jetting unit to jet the solution 4 (not shown) to the cell 1. Specific structures of the solution jetting nozzle 13 and the liquid pump 14 are arbitrary, and various structures may be applied to jet a predetermined amount of the solution 4 in a predetermined direction. For example, the liquid pump 14 may be structured with a piston that has a diameter of several millimeters to compression transport a substantially determinate amount of the solution 4. The solution jetting nozzle 13 may be structured with a hollow needle that has an internal diameter of several μm to jet the determinate amount of the solution 4, which is compression transported by the liquid pump 14, in droplets in a direction of the length of the solution jetting nozzle 13.

In the first embodiment, if the laser 6 is irradiated perpendicularly to the moving table 11, the solution 4 cannot be jet in a direction that is perpendicular to the direction in which the laser 6 is irradiated because the solution jetting nozzle 13 cannot be arranged completely horizontally to the moving table 11 due to a side edge of the petri dish 23. An example in which the solution 4 is jet in the direction perpendicular to the direction in which the laser 6 is irradiated is explained later in a third embodiment. A kind of the solution 4 to be jet is arbitrary. For example, the solution 4 may be a gene solution that includes a gene, or a drug solution that includes a drug. The nozzle moving table 15 is a unit to move the solution jetting nozzle 13, and is movable in the directions X and Y. The nozzle controlling unit 16 controls the movement of the nozzle moving table 15. The pump controlling unit 17 controls the liquid pump 14.

The laser irradiation device 18 irradiates the laser 6 to the cell 1 to form the opening 7 (not shown in FIG. 2) through which the solution 4 jet from the solution jetting nozzle 13 is introduced inside the cell 1. A specific structure of the laser irradiation device 18 is arbitrary. For example, a near-infrared pulsed laser (an Nd:YAG laser, a Ti:Sapphire laser) may be applied to the laser irradiation device 18. If such pulsed laser is used, it is possible to irradiate the laser 6 at each jetting of the solution 4. The laser controlling unit 19 controls the irradiation of the laser 6 by the laser irradiation device 18 based on an instruction from the central controlling unit 22.

The observation device 20 is an image pickup unit that includes units to obtain images such as a microscope and a CCD camera. The image processing unit 21 analyzes and processes the images obtained by the observation device 20. In the first embodiment, particularly, the observation device 20 and the image processing unit 21 function as a relative-distance calculating unit that calculates a relative distance between the cell 1 and the solution jetting nozzle 13.

The central controlling unit 22 is electrically connected to the table controlling unit 12, the pump controlling unit 17, the nozzle controlling unit 16, the laser controlling unit 19, and the image processing unit 21 as shown, and controls each of these units. In the first embodiment, particularly, the central controlling unit 22 functions as a timing controlling unit that controls timing in which the laser 6 is irradiated based on the relative distance between the cell 1 and the solution jetting nozzle 13 calculated by the observation device 20 and the image processing unit 21.

Figure 8:
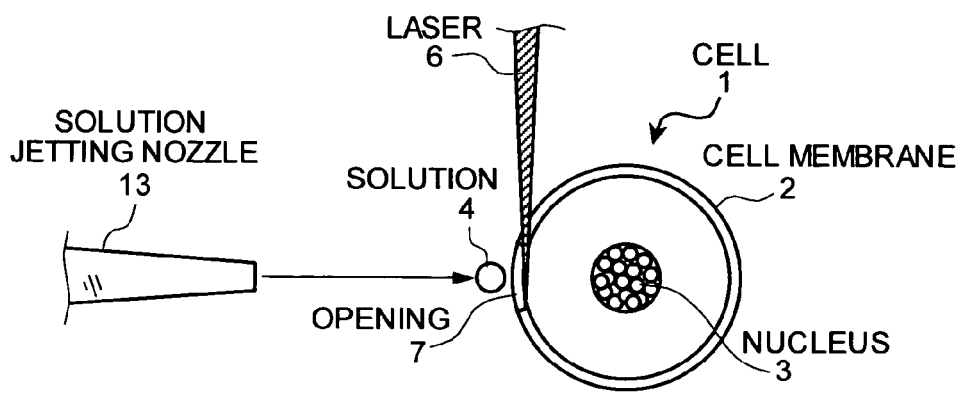
Figure 9:
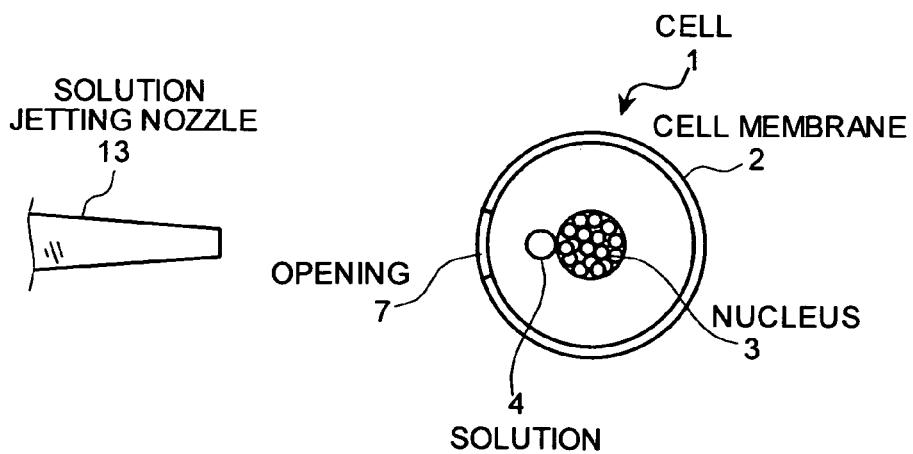
Figure 10:
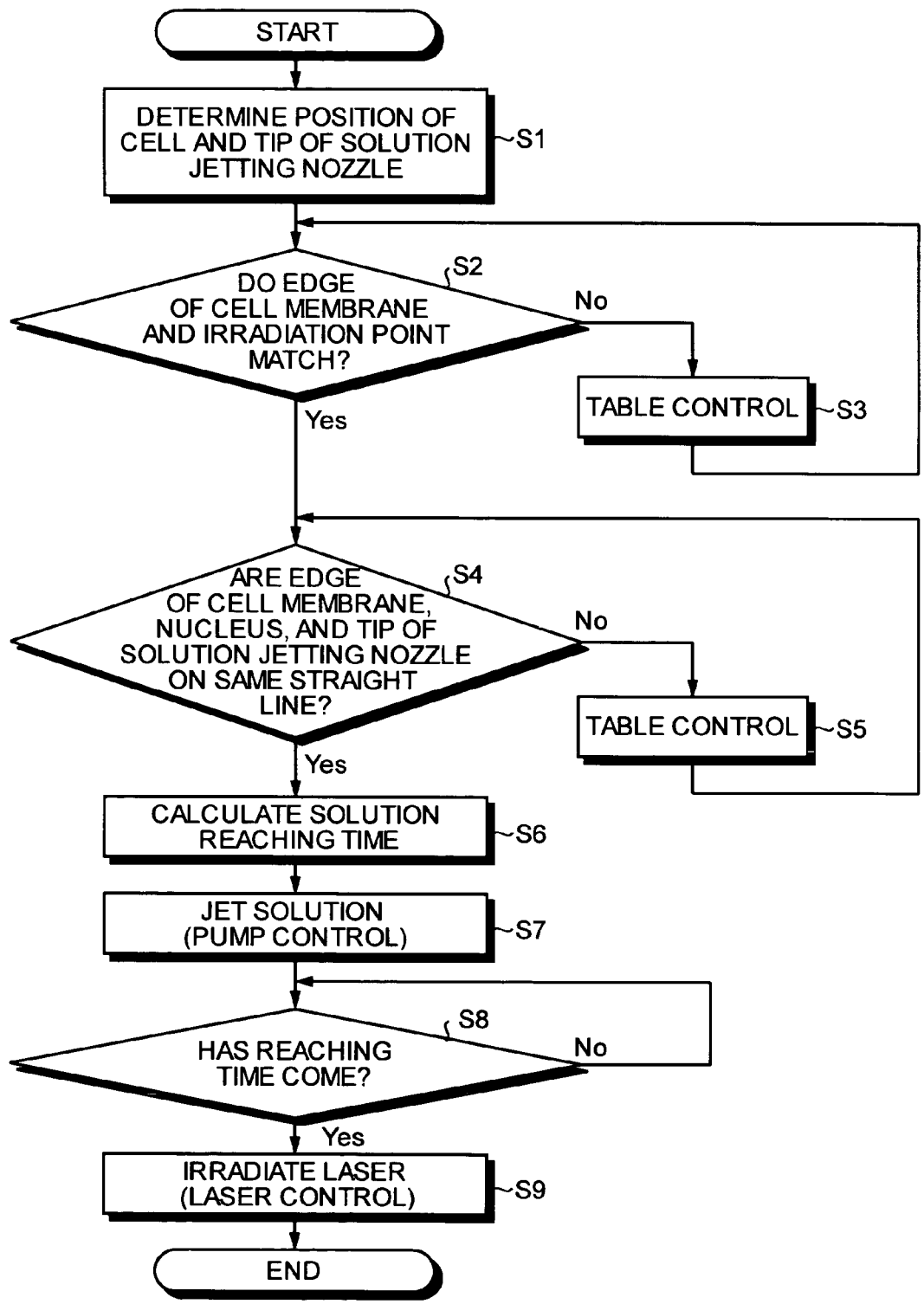
FIG. 10 is a flowchart of a solution injecting process according to the first embodiment.

Concretely how the solution is injected into the cell with the apparatus 10 is explained next. FIGS. 3 to 9 are diagrams for sequentially explaining a process of the solution injection according to the first embodiment. FIG. 10 is a flowchart of the process of the solution injection according to the first embodiment. First, an operator places the petri dish 23 that includes the cell cultivation solution on the moving table 11. The cell 1 is anchored on the surface of the petri dish 23 inside. The solution jetting nozzle 13 is moved with the nozzle moving table 15 in such a manner that the tip of the solution jetting nozzle 13 is arranged near the cell 1.

Figure 3:
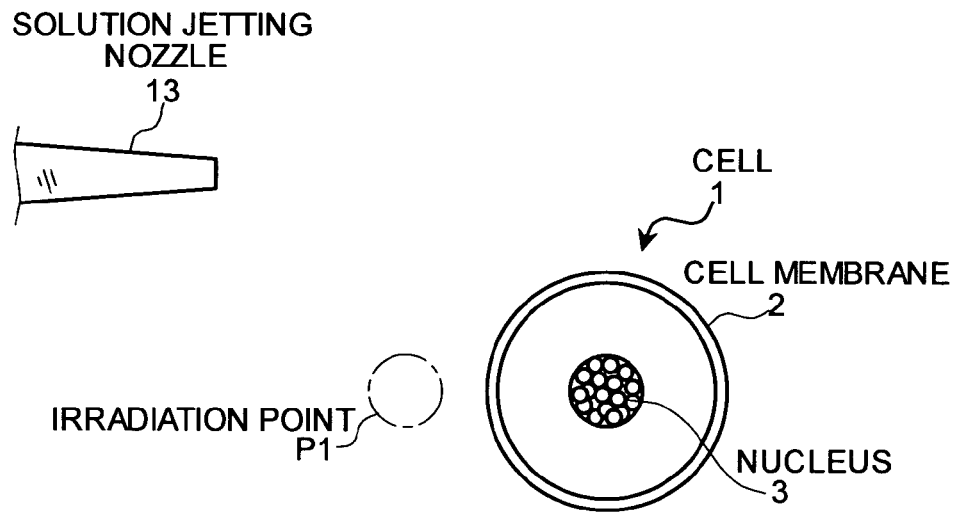
FIGS. 3 to 9 are diagrams for explaining the process of the solution injection according to the first embodiment.
Figure 4:
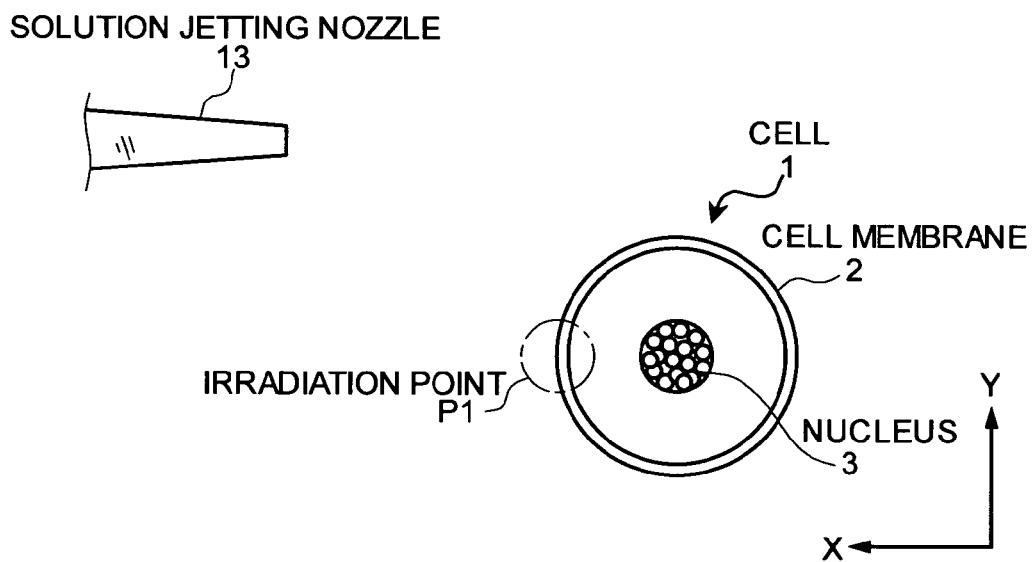
Figure 5:
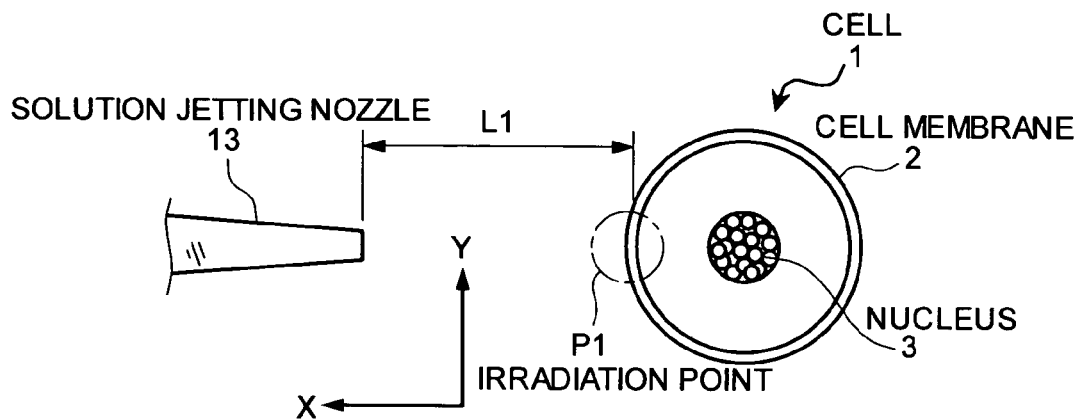
Figure 6:
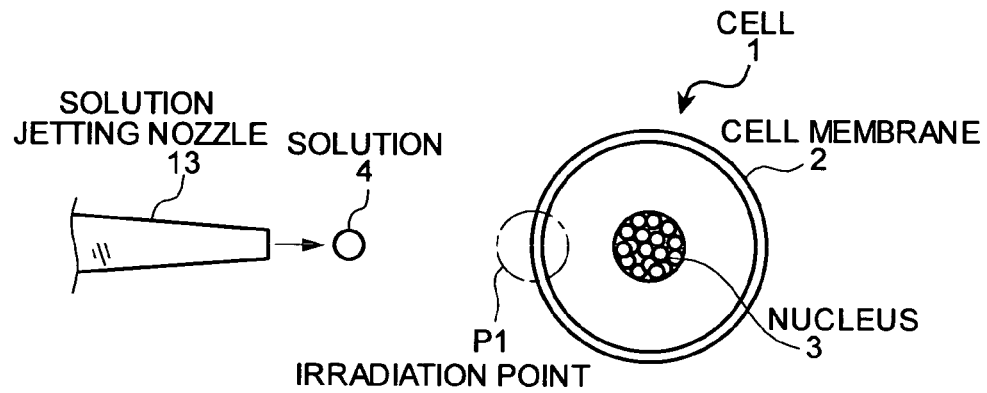
Figure 7:
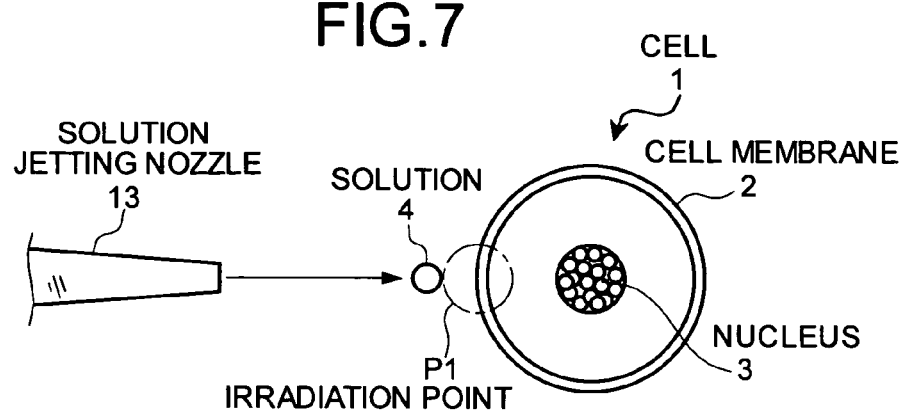

Then, an image of the cell 1 and areas around the cell 1 is obtained by the observation device 20. As a result, as shown in FIG. 3, the cell 1 and the tip of the solution jetting nozzle 13 are observed. For example, a center of the cell (a position of the nucleus 3) is easily determined if the rim of the cell 1 is determined. In FIGS. 3 to 9, a point to which the laser 6 is irradiated on the cell 1 is shown with a reference character "P1".

Then, the image obtained by the observation device 20 is image-processed by the image processing unit 21, thus, the positions of the cell 1 and the tip of the solution jetting nozzle 13 are determined (step S1 in FIG. 10). The point P1 shown in the picked-up image is set in advance in a coordinate and the like, or determined based on a relative position of the laser 6 to the observation device 20. The central controlling unit 22 controls the table controlling unit 12 to move the moving table 11 in the directions X and Y in such a manner that the point P1 is positioned on a portion in the cell membrane 2 (steps S2, and S3 in FIG. 10). A relative position between the point P1 of the laser 6 and the observation device 20 is fixed, therefore, only the cell 1 is to be moved by moving the moving table 11.

Then, the central controlling unit 22 controls the nozzle controlling unit 16 to move the solution jetting nozzle 13 in the directions X and Y in such a manner that the tip of the solution jetting unit 13 is arranged at a proper position for jetting the solution 4 (steps S4, and S5 in FIG. 10). The proper position is a position that enables to jet the solution 4 toward the nucleus 3 of the cell 1, and that enables an arrangement in which the tip of the solution jetting nozzle 13, the point P1, and the nucleus 3 are substantially on a same straight line. Although in the first embodiment, the solution jetting nozzle 13 is moved in the directions X and Y, an arrangement may be provided to rotate the solution jetting nozzle 13 around a base of the solution jetting nozzle 13.

The central controlling unit 22 calculates time necessary for the solution 4 to reach the cell membrane 2 (step S6 in FIG. 10). Concretely, a distance (distance L1 shown in FIG. 5) between the tip of the solution jetting nozzle 13 and the cell membrane 2 of the cell 1 is calculated by processing the image, which is obtained by the observation device 20, by the image processing unit 21. A speed of the solution 4 jet from the solution jetting unit 13 is calculated in advance. The speed is determined based on factors such as concentrations of the cell cultivation solution and the solution 4, and pressure of the liquid pump 14. The central controlling unit 22 acquires a reaching time at which the solution 4 reaches the cell membrane 2 by calculating (distance L1/speed).

After the reaching time is calculated, the central controlling unit 22 controls the pump controlling unit 17 to drive the liquid pump 14 to jet the solution 4 from the solution jetting nozzle 13 (step S7 in FIG. 10). It is preferable that the solution 4 is jet in a form of a droplet in an amount necessary for only one of the cell 1 for the purpose of saving an amount of the solution 4 to be used to a minimum.

Upon jetting the solution 4, the central controlling unit 22 starts determining whether the reaching time has come (step S8 in FIG. 10). While the central controlling unit 22 is carrying out the determination above, the solution 4 jet travels in the direction in which the solution 4 is jet, and gradually approaches to the cell 1. When the reaching time comes, the central controlling unit 22 controls the laser controlling unit 19 to irradiate the laser 6 from the laser irradiation device 18 (step S9 in FIG. 10). Thus, the opening 7 is formed in the cell membrane 2 as shown in FIG. 8. In calculating and determining the reaching time, it is preferable that the timing is adjusted in such a manner that the opening 7 is formed the predetermined time before the solution 4 reaches the cell membrane 2 by adjusting the reaching time for several microseconds. Then, as shown in FIG. 9, the solution 4 is introduced inside the cell 1 through the opening 7. Thus the solution injection is completed.

Thus, in the first embodiment, the solution injection can be carried out regardless of a kind of the cell and a transfer substance, and regardless of number of times for which the solution injection is carried out because a needle is not used as in the conventional microinjection method, and therefore, even when the solution injection is carried out to a lot of the cells 1, the problem in which a part of the cell 1 adheres to the tip of the needle does not occur. Furthermore, the solution injection according to a microscopic structure of the cell 1 can be carried out because a shape and a position of the opening 7 can be controlled by controlling the laser 6. Moreover, because it is possible to inject the solution 4 into the cell 1 by propelling the solution 4, the solution injection can be achieved at higher efficiency and at lower cost compared a case in which the solution injection is carried out by the Brownian movement as in the conventional laser injection method.

Figure 11:
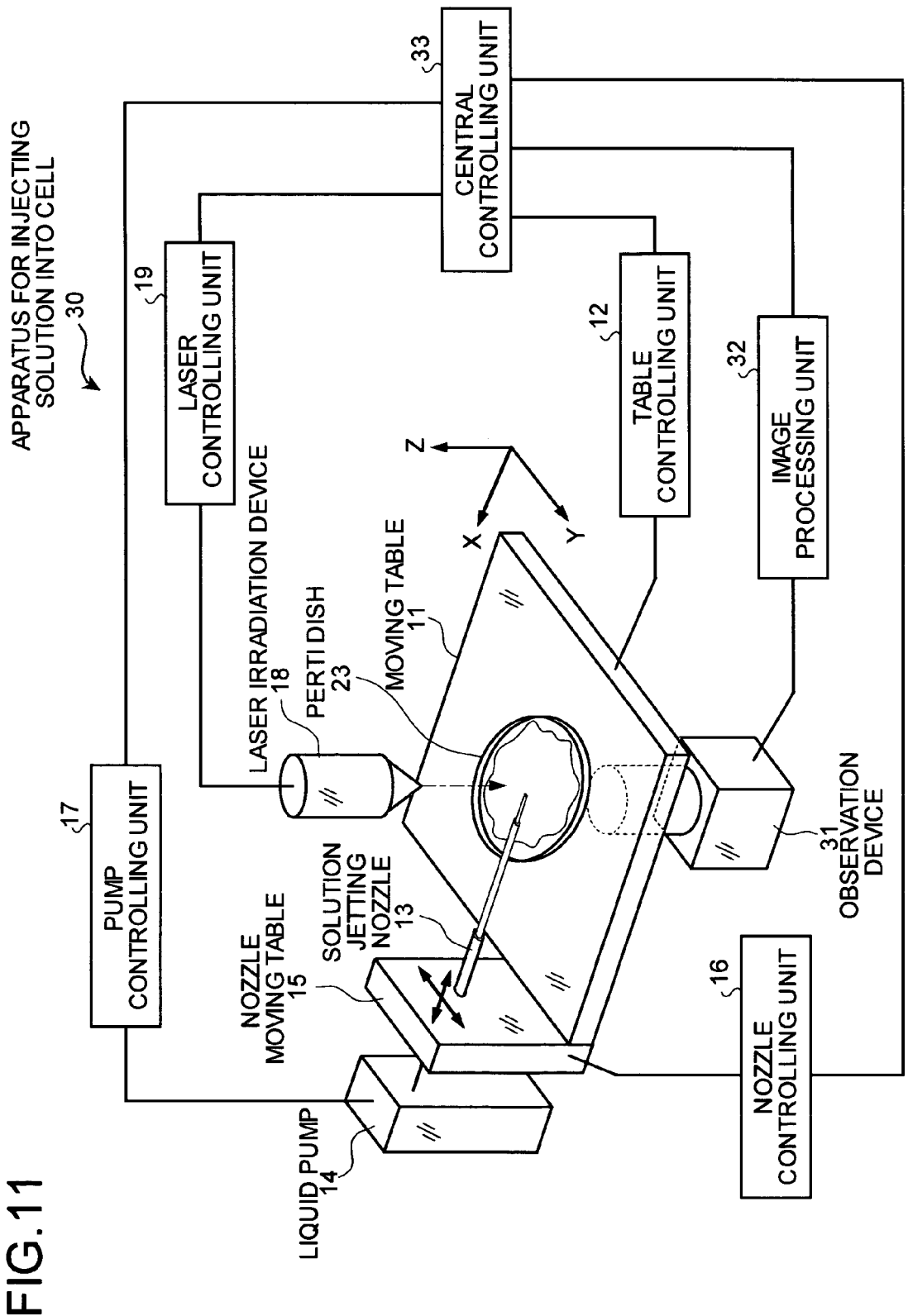
FIG. 11 is a configuration of an apparatus for injecting a solution into a cell according to a second embodiment.

An apparatus 30 for injecting a solution into a cell according to a second embodiment is explained next. FIG. 11 is a configuration of the apparatus 30 according to the second embodiment. Structures and methods not particularly mentioned are same as the structures and the methods in the first embodiment, and like reference characters are given to like components and like process steps in explanation below. The apparatus 30 includes an observation device 31, an image processing unit 32, and a central controlling unit 33 instead of the observation device 20, the image processing unit 21, and the central controlling unit 22 that are in the first embodiment.

The observation device 31 is an image pickup unit to obtain an image of the cell 1, the tip of the solution jetting nozzle 13, and the solution 4 jet to determine position of each of the above, and is structured, for example, as a differential interference contrast microscope or a phase contrast microscope. The solution 4 that includes a gene or a drug has a different refractive index from a refractive index of the cell cultivation solution in the petri dish 23. Therefore, the position of the solution 4 can be determined by analyzing change of an optical phase based on change of the refractive index. The image processing unit 32 is to determine the positions of the cell 1, the tip of the solution jetting nozzle 13, and the solution 4 jet by processing the image obtained by the observation device 31. In the second embodiment particularly, the observation device 31 and the image processing unit 32 function as a solution-position detecting unit that detects the positions of the cell 1 and the solution 4 jet by the solution jetting unit 13.

The central controlling unit 33 is electrically connected to the table controlling unit 12, the nozzle controlling unit 16, the pump controlling unit 17, the laser controlling unit 19, and the image processing unit 32 as shown, and controls each of these units. In the second embodiment particularly, the central controlling unit 33 function as a timing controlling unit that controls timing at which the irradiation of the laser 6 is carried out based on the positions of the cell 1 and the solution 4, which are calculated by the observation device 31 and the image processing unit 32.

Figure 12:
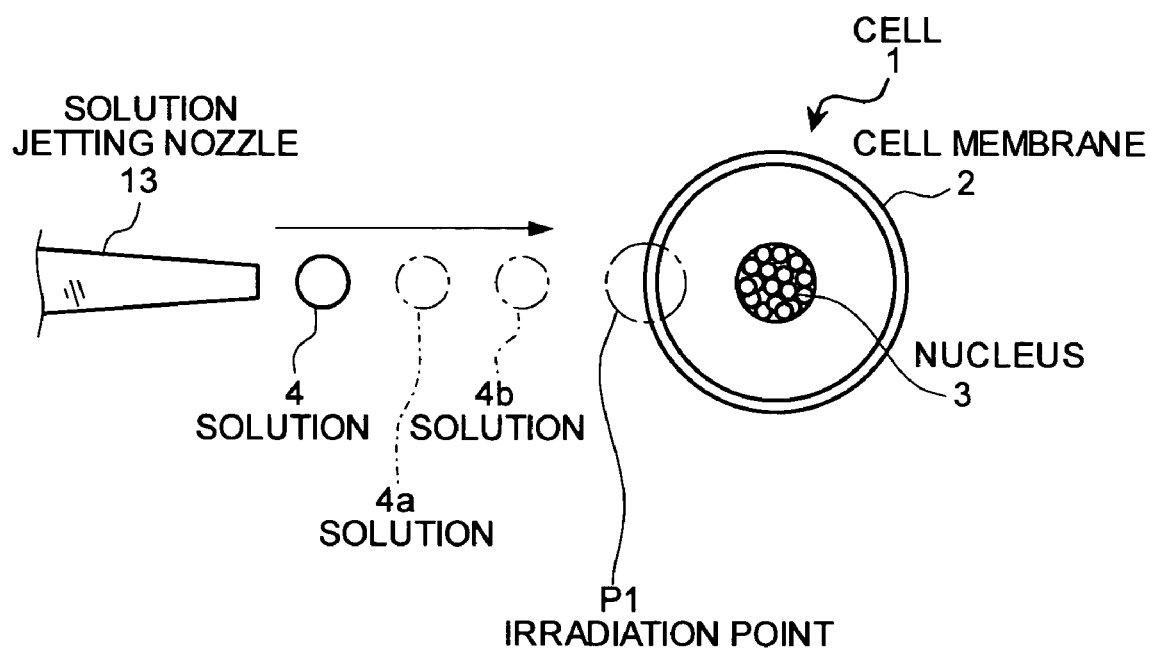
FIG. 12 is a diagram for explaining a process of solution injection according to the second embodiment.
Figure 13:
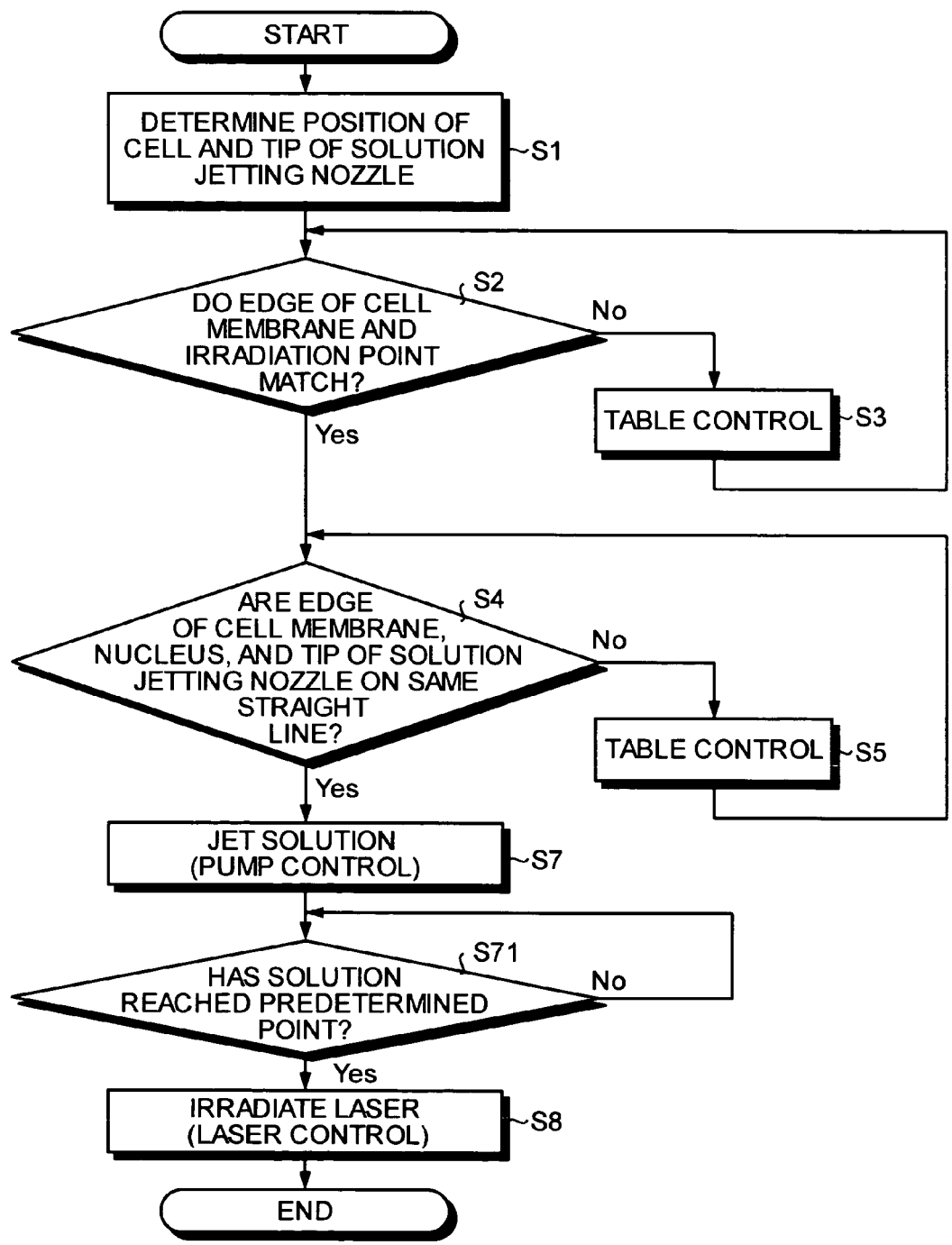
FIG. 13 is a flowchart of a solution injecting process according to the second embodiment.

A specific method of the solution injection with the apparatus for injecting a solution into a cell is explained next. FIG. 12 is a diagram for explaining a process of the solution injection according to the second embodiment. FIG. 13 is a flowchart of the process of the solution injection according to the second embodiment.

Positioning of the solution jetting nozzle 13 is carried out in the same way as the steps S1 to S5 in the first embodiment (steps S1 to S5 in FIG. 13). Then, the central controlling unit 33 controls the pump controlling unit 17 and drives the liquid pump 14 to jet the solution 4 from the solution jetting nozzle 13 (step S7 in FIG. 13). Upon jetting the solution 4, the central controlling unit 33 starts checking the position of the solution 4 that is determined by the image processing unit 32 based on the image obtained by the observation device 31. The solution 4 jet in a droplet travels toward the cell 1 in the cell cultivation solution. While traveling, because there is a slight difference in the refractive index between the solution 4 and the cell cultivation solution, the optical phase changes. Therefore, progress of the solution 4 (the position of the solution 4) in the cell cultivation solution can be determined in real time by observing the change of the phase.

The central controlling unit 33 determines the position of the solution 4 (step S71 in FIG. 13). The solution 4 progresses to a position of a solution 4*a* and then a position of a solution 4*b* in FIG. 12, and when the solution 4 reaches the cell membrane 2 of the cell 1, or a predetermined time before the solution 4 reaches the cell membrane 2, the central controlling unit 33 controls the laser controlling unit 19 to irradiate the laser 6 by the laser irradiation device 18 (step S8 in FIG. 13). Thus, the opening 7 is formed in the cell membrane 2, and through the opening 7, the solution 4 is introduced into the cell 1. Thus, the solution injection is completed.

As described above, in the second embodiment, because the position of the solution 4 is observed in real time to determine the timing for irradiating the laser 6, the process to acquire the speed of the solution 4 is not necessary. Therefore, in addition to the effect in the second embodiment, it becomes possible to carry out the solution injection more easily.

Figure 14:
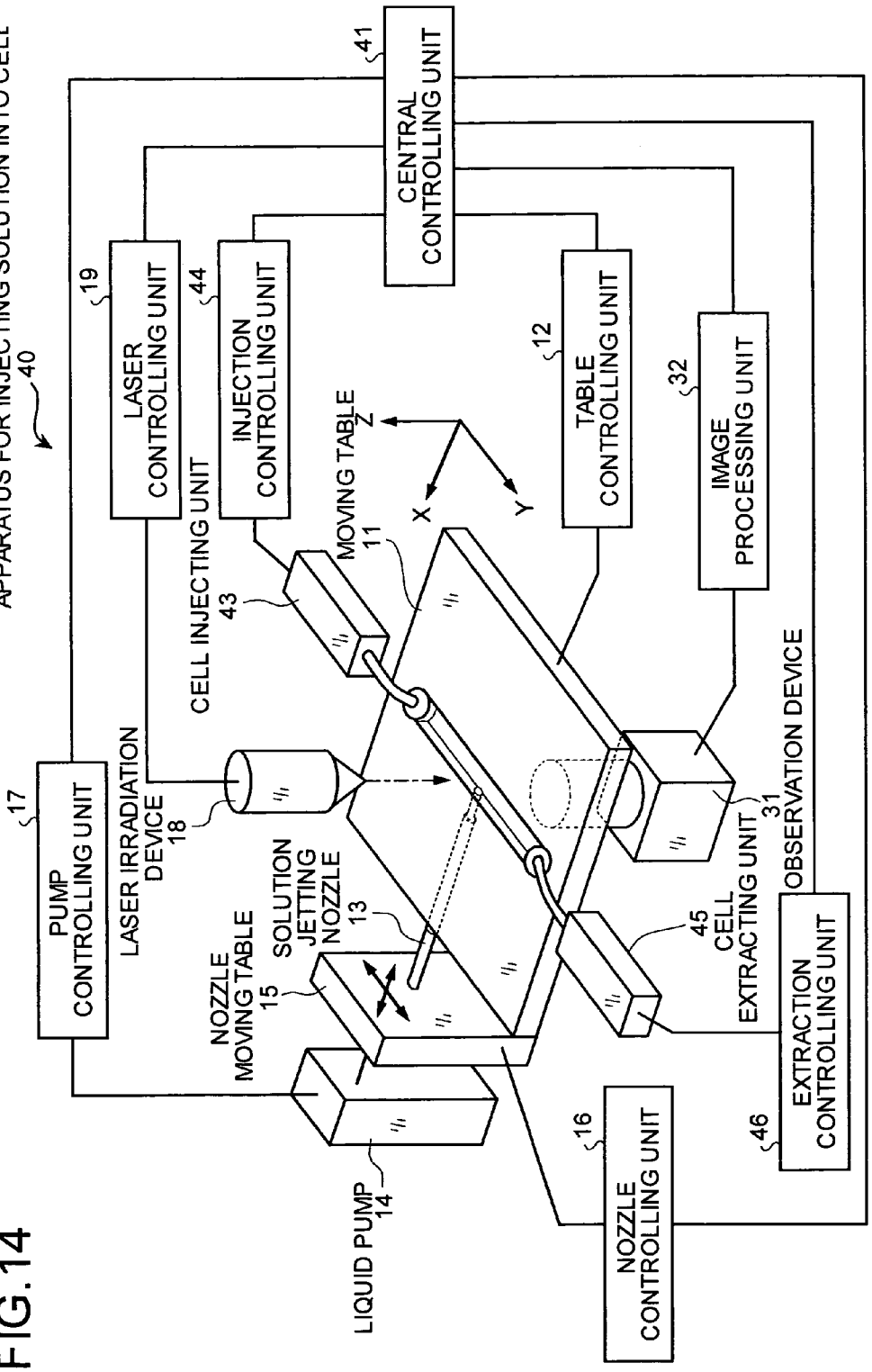
FIG. 14 is a configuration of an apparatus for injecting a solution into a cell according to a third embodiment.

An apparatus 40 for injecting a solution into a cell according to a third embodiment is explained next. FIG. 14 is a configuration of the apparatus 40 for injection solution into a cell. Structures and methods not particularly mentioned are same as the structures and the methods in the second embodiment, and like reference characters are given to like components and like process steps in explanation below. The apparatus 40 includes a central controlling unit 41 instead of the central controlling unit 33 in the second embodiment. The apparatus 40 further includes a flow path 42, a cell injecting unit 43, an injection controlling unit 44, a cell extracting unit 45, and a extraction controlling unit 46.

The flow path 42 is a path in which the cell cultivation solution flows, and is formed as a rectangular-shaped groove as shown. The cell injecting unit 43 injects the cell cultivation solution in the flow path 42, and has a syringe-like structure. The injection controlling unit 44 controls injection of the cell by the cell injecting unit 43. The cell extracting unit 45 is to extract the cell cultivation solution from the flow path 42, and has, for example, a syringe-like structure. The extraction controlling unit 46 controls extraction of the cell by the cell extracting unit 45.

Figure 15:
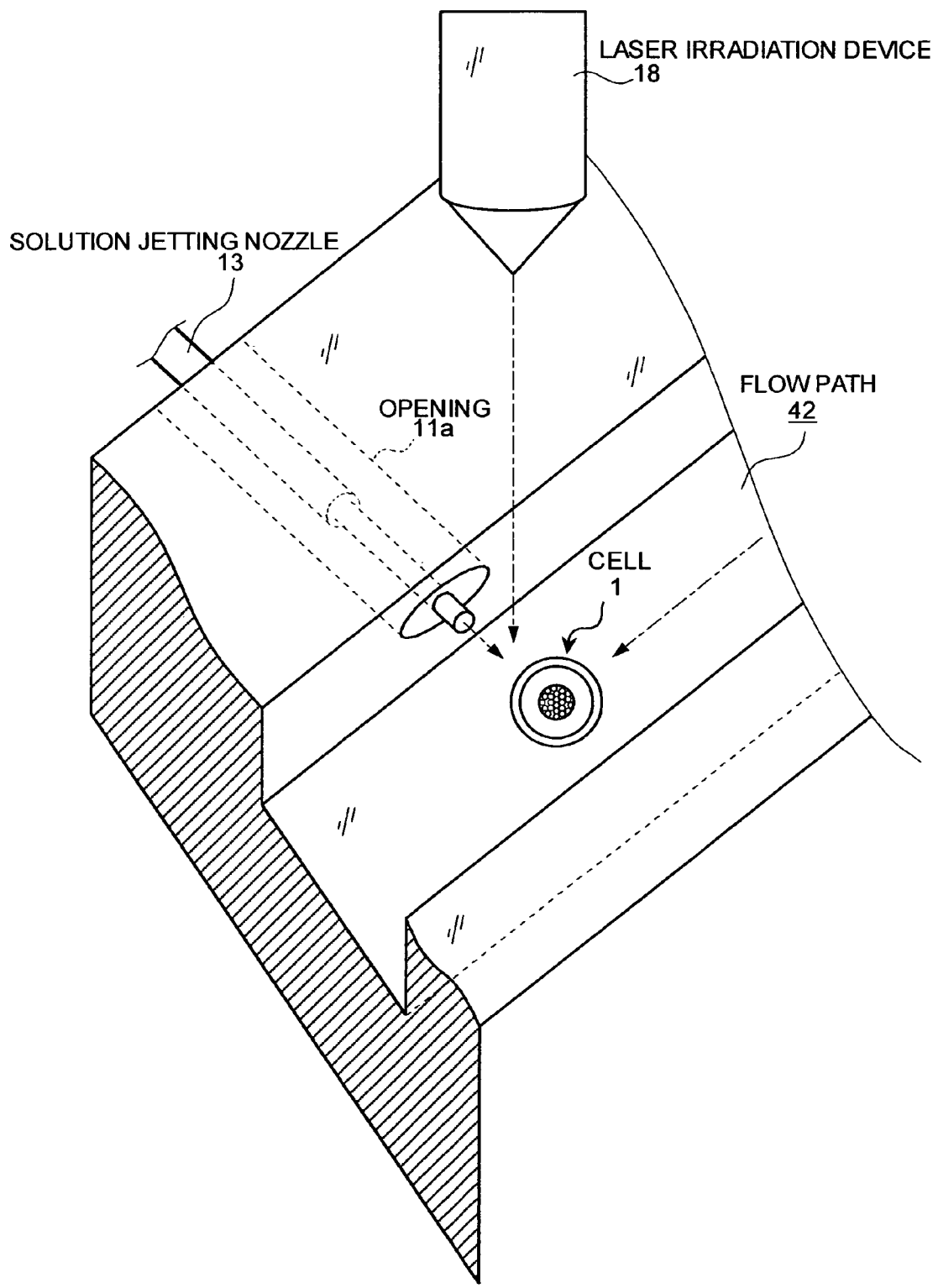
FIG. 15 is a perspective view for explaining an arrangement of a solution jetting nozzle according to the third embodiment.
Figure 16:
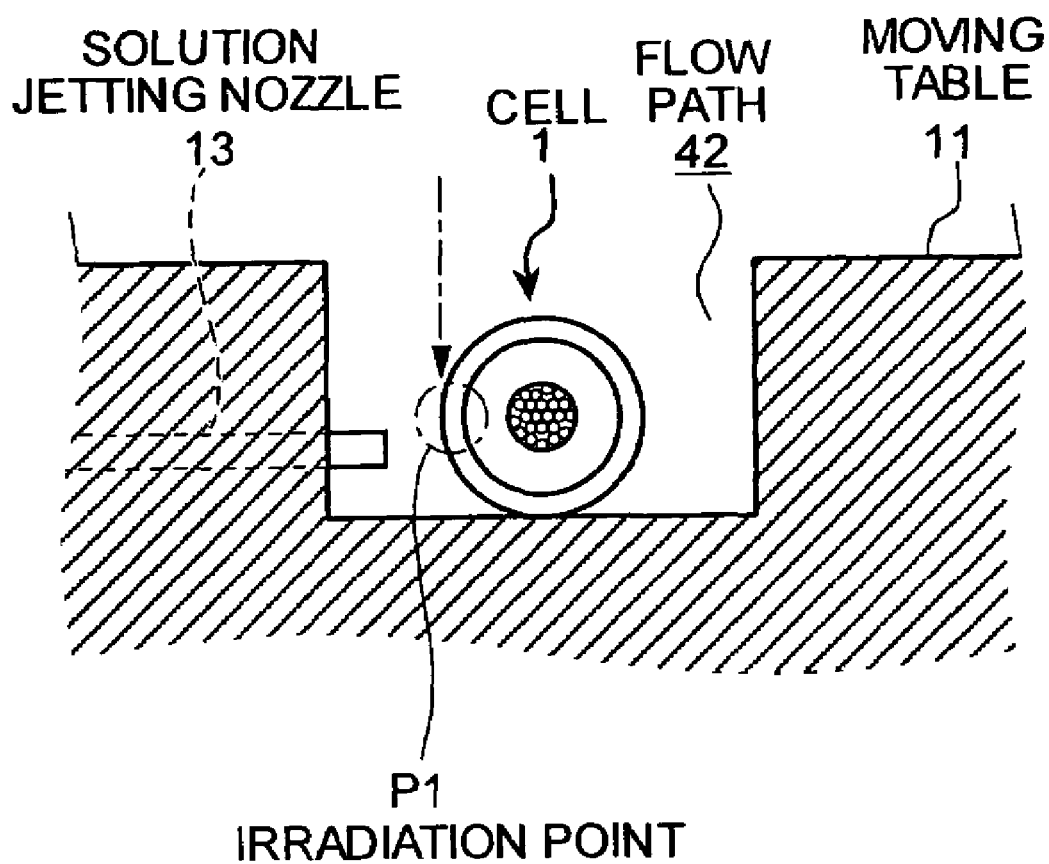
FIG. 16 is a longitudinal cross-section for explaining the arrangement of the solution jetting nozzle according to the third embodiment.

Arrangement of the solution jetting nozzle 13 is explained next. FIG. 15 is a perspective view for explaining the arrangement of the solution jetting nozzle 13. FIG. 16 is longitudinal cross-section for explaining the arrangement. As shown in FIGS. 15 and 16, the solution jetting nozzle 13 is arranged substantially horizontally to the moving table 11. Concretely, an opening 11*a* is formed substantially horizontally to the moving table 11. The solution jetting nozzle 13 is arranged in such a manner that the tip of the solution jetting nozzle 13 opens inside the flow path 43 through a side of the moving table 11 and through the opening 11*a*. This arrangement enables to jet the solution 4 in the direction substantially perpendicular to the direction in which the laser 6 is irradiated, if the laser 6 is irradiated in a direction perpendicular to the moving table.

A cell trapping unit, not shown, that traps the cell 1 that flows inside the flow path 42 is arranged at a position that corresponds to the tip of the solution jetting nozzle 13 in the flow path 42. A specific structure of the cell trapping unit is arbitrary. For example, the cell trapping unit may be structured with an opening (not shown) that has a smaller diameter than a diameter of the cell arranged in the flow path 42 to trap the cell 1 by sucking the cell 1 with a suction device. The point P1 at which the laser is irradiated by the laser irradiation device 18 is determined at a point on the cell membrane 2 of the cell 1 trapped by the cell trapping unit as shown in FIG. 16.

A specific method of the solution injection with the apparatus 40 is explained next. First, the central controlling unit 41 controls the injection controlling unit 44 to drive the cell injecting unit 43. The cell injecting unit 43 injects the cell cultivation solution in the flow path 42 (step S10 in FIG. 17). Then, the central controlling unit 41 determines whether the cell 1 is trapped by the cell trapping unit based on an image that is obtained by the observation device 31, and is image-processed by the image processing unit 32 (step S11 in FIG. 17). It is possible to determine whether the cell 1 is trapped by the cell trapping unit based on the difference in the refractive index between the cell 1 and the cell cultivation solution.

Figure 17:
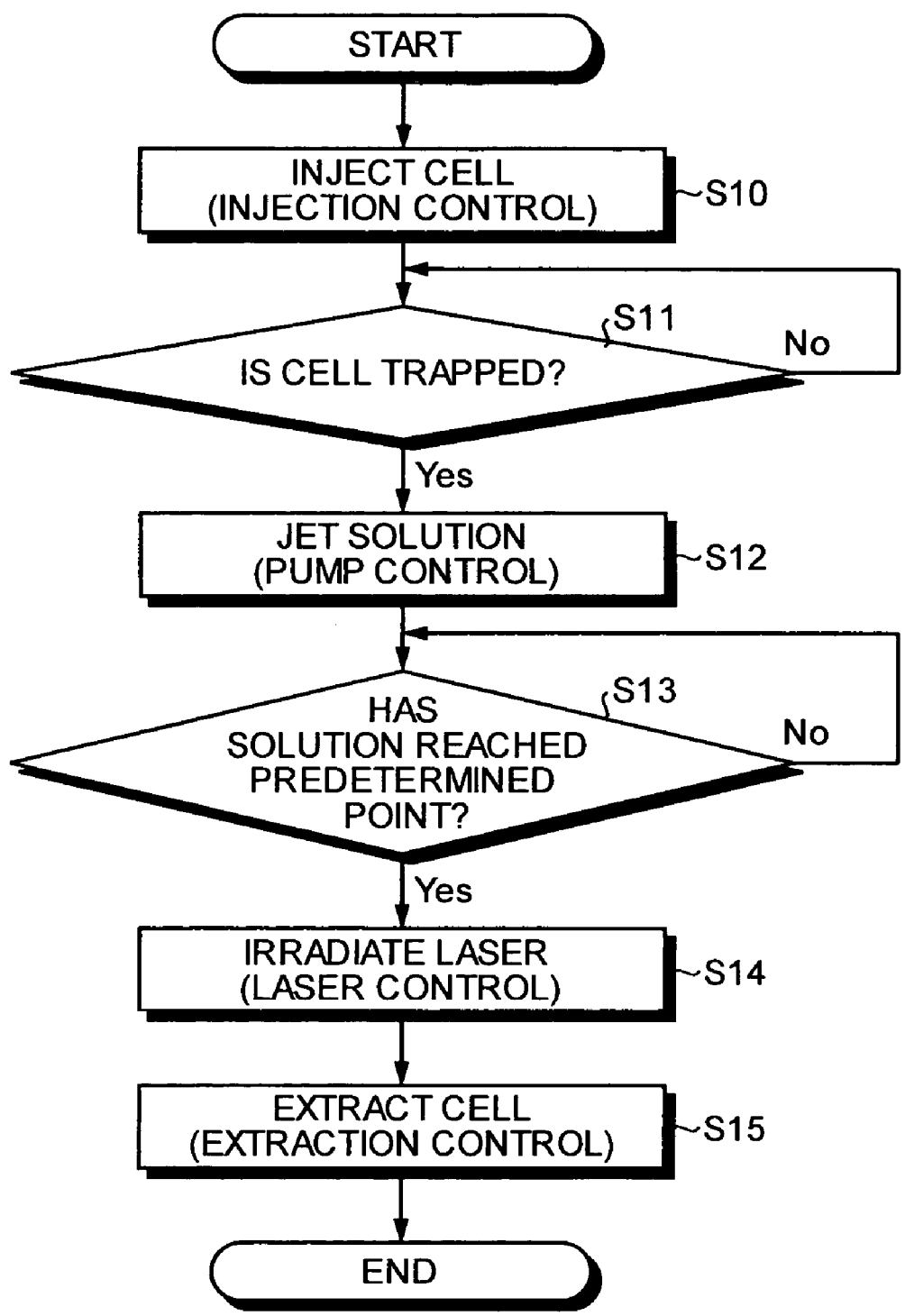
FIG. 17 is a flowchart of a solution injecting process according to the third embodiment.

When the cell 1 is trapped, the central controlling unit 41 controls the pump controlling unit 17 to drive the liquid pump 14 to jet the solution 4 from the solution jetting nozzle 13 (step S12 in FIG. 17). Upon jetting the solution 4, the central controlling unit 41 starts observing the progress of the solution 4 jet in real time based on the image, which is obtained by the observation device 31 and is image-processed by the image processing unit 32.

The central controlling unit 41 determines the position of the solution 4 (step S13 in FIG. 17), and when the solution 4 reaches the cell membrane 2 of the cell 1, or the predetermined time before the solution 4 reaches the cell membrane 2, the central controlling unit 41 controls the laser controlling unit 19 to irradiate laser 6 by the laser irradiation device 18 (step S17 in FIG. 17). Thus, the opening 7 is formed in the cell membrane 2, and through the opening 7, the solution 4 is introduced into the cell 1. Thus, the solution injection is completed. After releasing the cell 1 from the cell trapping unit as necessary, the central controlling unit 41 controls the extraction controlling unit 46 to drive the cell extracting unit 45. The cell extracting unit 45 extracts the cell cultivation solution from the flow path 42 (step S15 in FIG. 17).

As described above, in the third embodiment, because the solution jetting nozzle 13 is arranged substantially horizontally to the moving table 11 in such a manner that the tip of the solution jetting nozzle opens inside the flow path 42, it is possible to jet the solution 4 from sideward of the cell 1. Therefore, in addition to the effect in the second embodiment, it becomes possible to jet the solution 4 in a direction toward the nucleus 3 of the cell 1 at a further effective angle.

While the first to third embodiments according to the present invention have been explained, specific structures and methods of the present invention may be arbitrarily modified or improved within a scope of each of the technical ideas that are described in claims. Moreover, problems to be solved by the present invention and effects of the present invention are not to be limited to the description above, and the present invention may solve other problems not described above, or may have other effects not described above, or the present invention may solve a part of the problems described above, or may have a part of the effects described above.

The cell includes a cell-like minute particle. Moreover, all or a part of the control explained as the control that is automatically carried out in each of the embodiments above may be carried out manually. Furthermore, the timing of the irradiation of the laser 6, and the timing of the jet of the solution 4 is not necessarily required to be determined at every solution injection, and an average timing may be uniformly applied.

According to an aspect of the present invention, it is possible to carry out the solution injection regardless of a kind of the cell and a transfer substance, and regardless of number of time for which the solution injection is carried out. Furthermore, because a shape and a position of the opening can be adjusted by adjusting the laser, the solution injection according to a microscopic structure of the cell becomes possible. Moreover, because the solution is given the propulsive force, and is injected into the cell by the propulsive force, efficiency in injecting the solution becomes high, and cost for the solution injection can be reduced.

Furthermore, the solution jet is injected into the cell through the opening that is in the direction to which the solution is traveling, it is possible to inject the solution efficiently.

Moreover, by jetting the solution in the form of droplets, it is possible to save an amount of the solution to be used to a minimum.

Furthermore, if the laser is irradiated in a direction that is substantially perpendicular to a direction that is same as a direction of a line that connects the nucleus of the cell and a point on a cell membrane of the cell at which the opening is to be formed, it is possible to reduce possibility to damage the nucleus. Therefore, productivity in the solution injection improves.

Moreover, if the solution is jet in a direction that is same as a direction of the line that connects the nucleus of the cell and the point on the cell membrane of the cell at which the opening is to be formed and a direction that is substantially perpendicular to the direction in which the laser is irradiated, the solution can be jet toward the nucleus to the opening from the front. Therefore, it is possible to inject the solution more smoothly.

Furthermore, the laser can be irradiated to the cell at a point of time that is before the solution reaches the cell, and that enables the solution to be injected before the opening to be formed in the cell becomes smaller by the self-repair mechanism of the cell. Therefore, it is possible to inject the solution smoothly and efficiently.

Moreover, it is possible to irradiate the laser at an appropriate timing according to a relative distance between the cell and the solution jetting unit, and the opening can be formed at an appropriate timing. Therefore, the solution can be injected smoothly and efficiently.

Furthermore, it is possible to irradiate the laser at an appropriate timing according to a position of the cell and a position of the solution, and the opening can be formed in an appropriate timing. Especially because a process to acquire a speed of the solution is not necessary, the solution injection can be carried out more easily. Moreover, because even the speed of the solution varies due to variation in viscosity of the cell cultivation solution or pressure of a pump, it is possible to determine the timing for the irradiation of the laser. Therefore, it is possible to carry out the solution injection more accurately. Furthermore, because a process to calculate a reaching time at which the solution reaches the cell is not necessary, it is possible to carry out the solution injection more speedily.

Moreover, if a flow path in a shape of a groove through which the cell passes is formed, and the solution jetting unit is arranged substantially horizontally inside the flow path, the solution can be jet from the sideward of the cell. Therefore, it is possible to jet the solution to the nucleus of the cell at further effective angle.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. An apparatus for injecting a solution into a cell, comprising:
   a solution jetting unit that jets a solution toward a cell;
   a laser irradiating unit that irradiates a laser to the cell to form an opening in the cell through which the solution is introduced into the cell;
   a timing controlling unit that controls timing of irradiation by the laser irradiating unit, wherein the timing controlling unit controls the timing of the irradiation so as to form the opening at a point of time in which the solution reaches the cell, or a predetermined time before the point of time in which the solution reaches the cell, and
   a solution-position detecting unit that detects a position of the cell and a position of the solution at least at a point of time when said solution is in transit from said solution jetting unit to the cell, wherein the timing controlling unit controls the timing of the irradiation of the laser based on the position of the cell and the position of the solution detected.

2. The apparatus according to claim 1, wherein the cell has a nucleus, and the laser irradiating unit forms the opening at a point on a surface of the cell such that the is applied on the nucleus.

3. The apparatus according to claim 1, wherein the solution jetting unit has an arrangement so that the solution is jet in droplets in the opening.

4. The apparatus according to claim 1, wherein the laser irradiating unit is a near-infrared pulsed laser.

5. The apparatus according to claim 1, wherein the laser irradiating unit irradiates the laser in a direction that is substantially perpendicular to a line that connects a nucleus of the cell and a point on a surface of the cell at which the opening is to be made.

6. The apparatus according to claim 1, wherein the solution jetting unit jets the solution in a direction that is same as a direction of a line that connects a nucleus of the cell and a point on a surface of the cell at which the opening is to be made, and the laser irradiating unit irradiates the laser at the point from a direction that is substantially perpendicular to the line.

7. The apparatus according to claim 1, further comprising a distance calculating unit that calculates a distance between the cell and the solution jetting unit, wherein the timing controlling unit controls the timing of the irradiation of the laser based on the distance calculated.

8. The apparatus according to claim 1, further comprising:
   a base; and
   a flow path that is formed in the base into a shape of a groove, and in which the cell passes through, wherein the solution jetting unit includes a nozzle for jetting the solution, and is arranged in such a manner that the nozzle is substantially horizontally to the base, and opens inside the flow path.

9. The apparatus according to claim 1,
   wherein the solution-position detecting unit detects a nozzle tip of the solution jetting unit as the position of the solution; and
   wherein the timing controlling unit calculates a timing when the solution reaches the cell based on a distance between the nozzle tip and the position of the cell.

* * * * *